United States Patent
Taylor et al.

(10) Patent No.: US 7,322,996 B2
(45) Date of Patent: Jan. 29, 2008

(54) PRECISELY GUIDED LANCET

(75) Inventors: William C. Taylor, Alpharetta, GA (US); Richard W. Levaughn, Talking Rock, GA (US); Mitchell Solis, Cumming, GA (US); Jeffrey T. Stout, Smyrna, GA (US)

(73) Assignee: Facet Technologies, LLC, Kennesaw, GA (US)

( * ) Notice: Subject to any disclaimer, the term of this patent is extended or adjusted under 35 U.S.C. 154(b) by 341 days.

(21) Appl. No.: 10/452,780

(22) Filed: May 30, 2003

(65) Prior Publication Data

US 2004/0098008 A1 May 20, 2004

Related U.S. Application Data

(60) Provisional application No. 60/384,468, filed on May 31, 2002.

(51) Int. Cl.
*A61B 17/32* (2006.01)
(52) U.S. Cl. ....................................... 606/181
(58) Field of Classification Search ........ 606/181–186; 600/573, 576, 566, 583; 30/329, 335–339
See application file for complete search history.

(56) References Cited

U.S. PATENT DOCUMENTS

| | | | |
|---|---|---|---|
| 1,135,465 A | | 4/1915 | Pollock |
| 1,487,791 A | * | 3/1924 | Manson ...................... 30/339 |
| 4,360,016 A | | 11/1982 | Sarrine |
| 4,388,925 A | | 6/1983 | Burns |
| 4,416,279 A | | 11/1983 | Lindner et al. |
| 4,503,856 A | | 3/1985 | Cornell et al. |
| 4,527,561 A | | 7/1985 | Burns |
| 4,627,445 A | | 12/1986 | Garcia et al. |
| 4,794,926 A | | 1/1989 | Munsch et al. |
| 4,858,607 A | | 8/1989 | Jordan et al. |

(Continued)

FOREIGN PATENT DOCUMENTS

EP 0 613 656 A2 9/1994

(Continued)

OTHER PUBLICATIONS

Sutor, Anton H. M.D., Bowie, E.J. Walter, B.M. B.Ch., Thomspon, John H. Jr., Ph.D., Didisheim, Paul, M.D., Mertens, Benny F., M.D., Owen, Charles A. Jr., M.D.; "Bleeding from Standardized Skin Punctures: Automated Technic for Recording Time, Intensity, and Pattern of Bleeding"; Quantitation of Bleeding; May 1971; J.C.P.; pp. 541-549; vol. 55; Rochester, Minnesota.

*Primary Examiner*—Anhtuan T. Nguyen
*Assistant Examiner*—Tuan V. Nguyen
(74) *Attorney, Agent, or Firm*—Gardner Groff Greenwald & Villanueva, PC

(57) ABSTRACT

A lancet having one or more portions of the shank of the lancet blade exposed for direct engagement with cooperating portion(s) of the lancet carrier of a lancing device. This direct engagement of the lancet blade with the lancet carrier provides more precise positional control of the location of the lancing site by eliminating the effect that any variation in the position of the lancet blade within the lancet body would otherwise have on the positioning of the lancet tip. Tolerance stack-up is thereby reduced and accuracy is improved, reducing the necessary sample size and minimizing pain resulting from the lancing operation.

2 Claims, 4 Drawing Sheets

U.S. PATENT DOCUMENTS

| | | | |
|---|---|---|---|
| 4,924,879 A | 5/1990 | O'Brien | |
| 4,976,724 A | 12/1990 | Nieto et al. | |
| 5,318,584 A | 6/1994 | Lange et al. | |
| 5,324,303 A | 6/1994 | Strong et al. | |
| 5,356,420 A | 10/1994 | Czernecki et al. | |
| 5,368,047 A | 11/1994 | Suzuki et al. | |
| 5,439,473 A | 8/1995 | Jorgensen | |
| 5,554,166 A | 9/1996 | Lange et al. | |
| 5,569,287 A | 10/1996 | Tezuka et al. | |
| 5,613,978 A | 3/1997 | Harding | |
| 5,628,765 A | 5/1997 | Morita | |
| 5,730,753 A | 3/1998 | Morita | |
| 5,741,288 A | 4/1998 | Rife | |
| 5,755,733 A * | 5/1998 | Morita | 606/182 |
| 5,857,983 A | 1/1999 | Douglas et al. | |
| 5,916,230 A | 6/1999 | Brenneman et al. | |
| 5,951,582 A | 9/1999 | Thorne et al. | |
| 5,971,941 A | 10/1999 | Simons et al. | |
| 6,042,595 A * | 3/2000 | Morita | 606/181 |
| 6,045,567 A | 4/2000 | Taylor et al. | |
| 6,306,152 B1 | 10/2001 | Verdonk et al. | |
| 6,364,890 B1 | 4/2002 | Lum et al. | |
| 6,602,268 B2 * | 8/2003 | Kuhr et al. | 606/181 |
| 6,866,641 B2 * | 3/2005 | Marshall | 600/583 |
| 2002/0004196 A1 | 1/2002 | Whitson | |
| 2002/0040230 A1 | 4/2002 | Kuhr et al. | |
| 2003/0109895 A1 * | 6/2003 | Taylor et al. | 606/181 |

FOREIGN PATENT DOCUMENTS

| | | |
|---|---|---|
| EP | 0589186 B1 | 3/1999 |
| EP | 0894471 A2 | 3/1999 |
| WO | WO 97/42886 | 11/1997 |
| WO | WO 00/76408 | 12/2000 |
| WO | WO 02/43591 A2 | 6/2002 |

* cited by examiner

PRECISELY GUIDED LANCET

CROSS-REFERENCE TO RELATED APPLICATION

This application claims the benefit of U.S. Provisional Patent Application Ser. No. 60/384,468, filed May 31, 2002; which application is incorporated herein by reference in its entirety for all purposes.

FILED OF THE INVENTION

The present invention relates generally to the field of medical devices, and more particularly to improved devices and methods for lancing the skin or other biological tissue of a human or animal subject to obtain a sample of blood or other body fluid for testing.

BACKGROUND OF THE INVENTION

Various lancing devices are known for penetrating the skin of a human or animal subject at a lancing site for obtaining a sample of blood or other body fluids. In general, a typical lancing device includes a housing containing a lancet connected to a spring-driven drive mechanism, and further includes a cocking mechanism for arming or energizing the drive-spring, and a trigger mechanism for releasing the drive mechanism to complete the lancing operation. Many lancing devices further include a depth-control mechanism for varying the depth of penetration, either by adjusting the distance of travel of the lancet tip, or by adjusting the position of an endcap through which the lancet protrudes during the lancing operation.

The lancet is typically a disposable component that can be releasably mounted in a cooperating lancet carrier that is operatively coupled to the drive mechanism of the lancing device. The used lancet typically is removed from the lancet carrier after sampling and disposed of. A new, sterile lancet is then replaced into the lancet carrier for further sampling. Most known lancets comprise a metal needle or blade (collectively referred to herein as a "lancet blade") with a sharp lancing tip. The lancet blade is typically embedded in a plastic body that has a size and shape configured for releasable engagement in the lancet carrier. The sharp tip of the lancet blade is typically embedded in a removable plastic shroud or cap to maintain sterility prior to use. Often, the endcap and the body of the lancet form a single, unitary plastic molding with a notched or necked section of reduced thickness for facilitating detachment and removal of the endcap.

Traditionally, a diabetic subject would use a lancing device to create a puncture wound in his/her skin at the desired sampling site, squeeze or "milk" the site to express a small sample droplet of blood, collect the sample droplet on a chemical test strip, insert the test strip in a blood glucose monitor for analysis, and review the test results. This procedure tends to be inconvenient and tedious, and the handling of small components may be difficult for subjects with impaired vision and manual dexterity. In order to encourage compliance with a prescribed sampling regimen, it is desirable to minimize the inconvenience resulting from the lancing procedure. Therefore, the market is tending to favor "all-in-one" devices that carry out the lancing, sample collection and sample analysis procedures in a single device.

Such all-in-one devices typically require precise alignment of the lancing site with the positioning of the sample collection media so that the user does not have to endure multiple lancet sticks or fumble with the test device to correct misalignments between the lancing site and the collection media. However, previously known lancing devices and lancets generally do not permit as precise control over the position of the lancing site as would be desired. This is often due to tolerance stacking resulting from slight variation in dimensions of the lancet blade, the plastic body of the lancet, the lancet carrier, the drive mechanism of the lancing device, the lancet housing, and/or other components, as well as the position of the lancet blade in the plastic body of the lancet. Individually, these dimensional variations may be small and within accepted manufacturing tolerances, but their aggregate effect sometimes results in a substantial misalignment of the lancing site and the location of the collection media delivered by an all-in-one sampling and test device. As a result, many all-in-one sampling and test devices are configured to generate a larger sample size than would otherwise be needed, in order to compensate for any such misalignments. However, generating a larger sample size typically requires that a larger wound be created during the lancing step, which adversely results in the infliction of more pain on the subject. Pain resulting from the lancing procedure often negatively affects patient compliance with a prescribed testing regimen, and is always sought to be minimized.

Accordingly, it can be seen that needs exist for devices and methods for enabling more precise guidance of a lancet, reducing tolerance stacking in the lancing procedure, and improving locational control of the of the puncture site. It is to the provision of devices and methods meeting this and other needs that the present invention is primarily directed.

SUMMARY OF THE INVENTION

Briefly described, the present invention facilitates precise locational control of the puncture site by providing a lancet with at least one exposed shank portion of the lancet blade for direct engagement with the lancet carrier of a lancing device, so that variations in the dimensions of the plastic body and in the positioning of the lancet blade in the plastic body do not affect the location of the puncture site. In further embodiments of the invention, at least two exposed shank portions of the lancet blade are provided, spaced a distance apart from one another, for engagement with the lancet carrier, to ensure proper alignment of the lancet blade more precise positioning of the lancet blade tip. By directly relating the position of the lancet blade tip to the lancet holding/driving means, several components of potential tolerance stack-ups are eliminated, resulting in a more precise puncture location.

In one aspect, the invention is a lancet for engagement within a lancet carrier portion of a lancing device. The lancet preferably includes a lancet blade mounted to a lancet body. The lancet blade preferably has a sharp tip and a shank, and at least a portion of the shank is exposed for direct engagement by the lancet carrier.

In another aspect, the invention is a lancet for releasable engagement in a lancing device. The lancet preferably includes a body portion and a lancet blade mounted within the body portion. The lancet blade preferably has a sharp tip extending outwardly from the body portion, and a shank having at least one exposed portion for direct engagement with a cooperating portion of the lancing device.

In yet another aspect, the invention is a lancet comprising a lancet blade having a sharp tip and a shank. The lancet blade is preferably mounted in a lancet body with at least a portion of the shank of the lancet blade exposed, and the exposed portion of the shank includes at least two positioning guides for direct engagement with a lancing device.

In still another aspect, the invention is a method of maintaining tight positional control of a lancing site location. The method preferably includes providing a lancet having at least one exposed shank portion; and mounting the lancet in a lancet carrier of a lancing device with the at least one exposed shank portion of the lancet in direct engagement with the lancing device.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWING FIGURES

DETAILED DESCRIPTION OF EXAMPLE EMBODIMENTS

Figure 1:
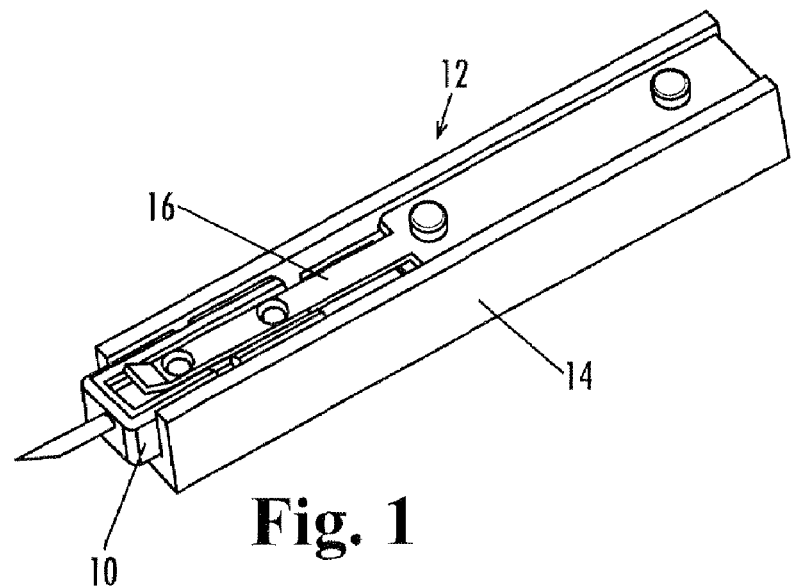
FIG. 1 is a perspective view of a lancet engaged in a lancet carrier portion of a lancing device according to an example embodiment of the present invention.
Figure 2:
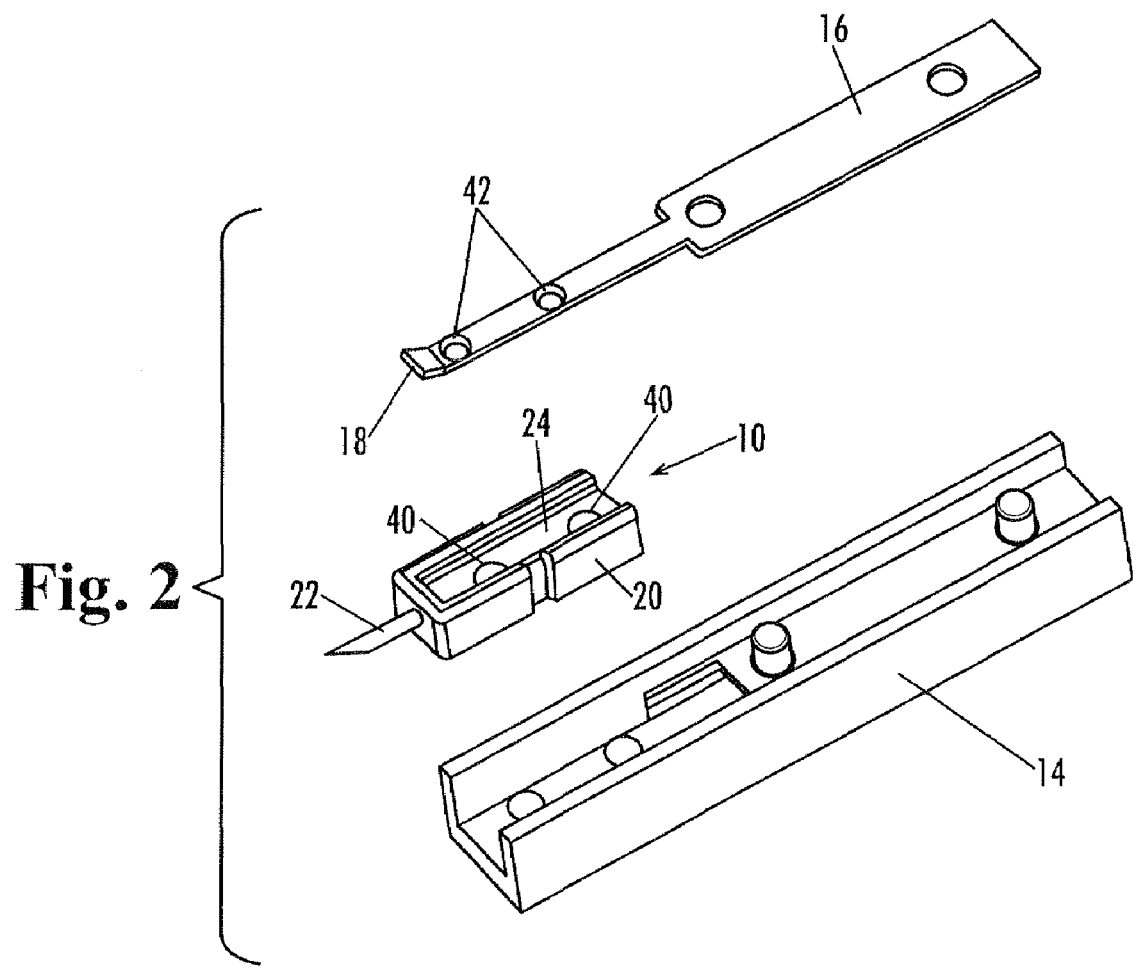
FIG. 2 is an exploded view of the lancet and lancet carrier of FIG. 1.
Figure 3:
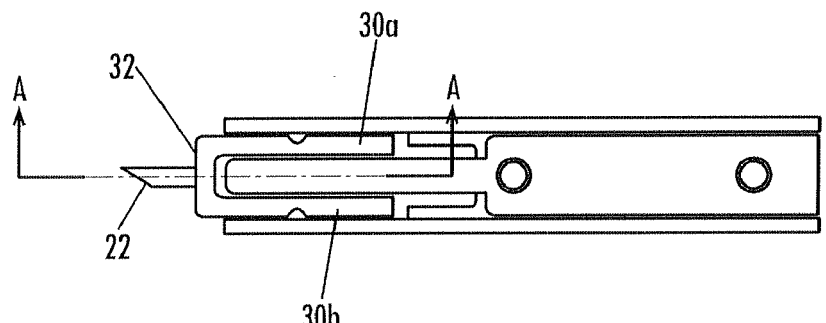
FIG. 3 is a top view of the lancet and lancet carrier of FIG. 1.
Figure 4:
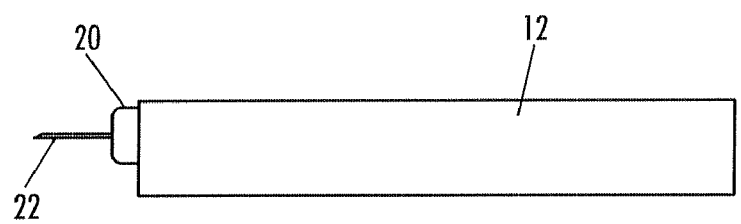
FIG. 4 is a side view of the lancet and lancet carrier of FIG. 1.
Figure 5:
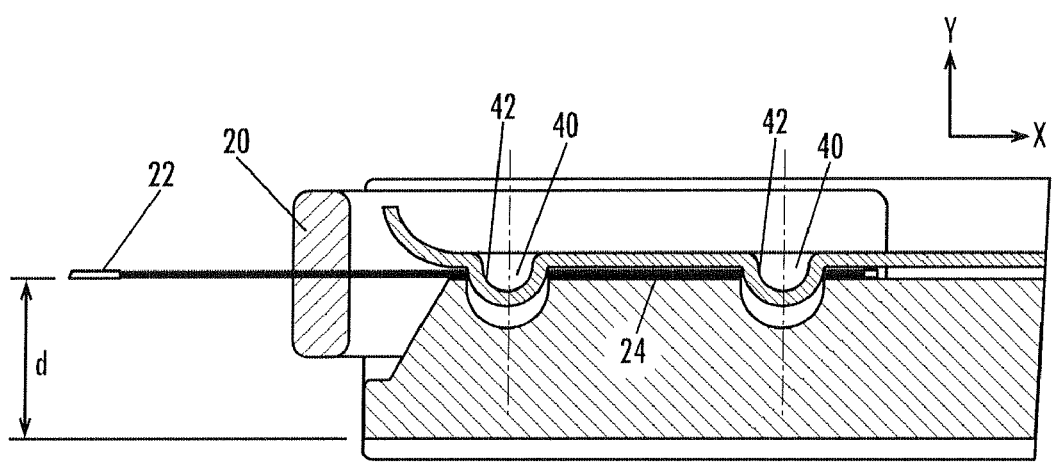
FIG. 5 is a detailed cross-sectional side view of the lancet and lancet carrier of FIG. 1, taken along section line A-A of FIG. 3.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

FIGS. 1-5 show a lancet 10 according to an example embodiment of the present invention, adapted for detachable engagement with a lancet carrier portion 12 of a lancing device. In the depicted embodiment, the lancet carrier 12 comprises a substantially rigid carriage 14 with a resilient arm 16 mounted thereto. A free end 18 of the arm 16 flexes away from the carriage 14 to receive and release the lancet 10, and is biased toward the carriage under its own resiliency to secure the lancet in position in the lancet carrier 12. The carriage 14 and arm 16 can comprise separate pieces connected by one or more pins of one piece engaged in holes of the other piece, by adhesive, welding, screws, clips, rivets, and/or by other connection means; or the carriage and arm can be fabricated as a unitary component. The lancet carrier 12 typically comprises a portion of a spring-driven piston of a lancing device of standard, known variety. Of course, those skilled in the art will recognize that the present invention is readily adapted to any of a wide variety of lancing devices.

The lancet 10 of the present invention preferably comprises an overmolding or body 20 of plastic or other substantially rigid material and a lancet blade having a sharp tip 22 and a shank portion 24. The lancet blade preferably comprises a section of flat material with generally rectangular cross-section, having a sharpened edge forming the tip 22. Alternatively, the lancet blade comprises a needle having a generally circular cross-section with a sharp tip, or a member of triangular, cross-shaped or other cross-sectional geometry. The lancet blade is preferably fabricated from a metal such as stainless steel, or a ceramic, polymeric or other material capable of holding a sharp tip or edge. The sharp tip 22 of the lancet blade is preferably sterilized and encapsulated or packaged to maintain sterility prior to use. For example, the tip 22 can be encapsulated in a removable plastic endcap that is molded with the plastic body 20 of the lancet.

At least a portion of the shank 24 is exposed for direct engagement with the lancet carrier 12. For example, in the depicted embodiment, the plastic body 20 of the lancet comprises a generally U-shaped body with two elongated legs 30a, 30b extending from an end panel 32 (see FIG. 3). The sharp tip 22 of the lancet blade extends outwardly through the end panel 32 opposite the legs 30, and substantially the entire shank 24 is exposed between the legs 30. In alternate embodiments, the shank 24 will be substantially embedded within the material of the body 20, with one or more holes, channels or openings formed in the body 20 to expose one or more smaller portion(s) of the shank 24.

In particularly preferred embodiments, at least two spaced apart portions of the shank 24 are exposed for engagement with cooperating positioning guides of the lancet carrier 12, to ensure correct alignment of the lancet 10 within the lancet carrier for greater positional control of the lancet tip 22 during the lancing operation. For example, in the depicted embodiment, two holes or recesses 40 are formed in exposed portions of the shank 24 at locations spaced a distance from one another along the lengthwise axis of the shank 24. Two spaced-apart projections or pins 42 extend outwardly from the free end 18 of the arm 16 of the lancet carrier 12, for cooperative engagement within the holes 40 when the lancet is mounted in the lancet carrier, as seen best in the cross-sectional view of FIG. 5. The carriage 14 preferably comprises cooperating recesses aligned to receive the projections 42. The direct-contacting engagement between the exposed shank portion of the lancet and the lancet carrier at two spaced-apart positions prevents misalignment by twisting or pivoting of the lancet within the lancet carrier, and thereby maintains more accurate positional control of the lancet tip. And because the pins 42 extend into the holes 40, the lancet is positively engaged to resist translational movement of the lancet blade relative to the lancet carrier in the plane of the lancet blade, as well as out of the plane of the blade. Of course, those skilled in the art will recognize that the lancet may comprise one or more pins or projections and the lancet carrier comprise one or more cooperating holes or recesses; and/or other forms of positioning guides may be utilized to provide direct engagement between the lancet blade and the lancet carrier of the lancing device.

In alternate embodiments, one or more exposed portions of the shank of the lancet blade protrude outwardly of the plastic body of the lancet in one or more directions forming one or more wing(s) for engagement with the lancet carrier to closely guide the unit and maintain positional control of the lancing site. In further alternate embodiments, the blade material is bent in different configurations to provide one or more exposed portions forming guiding geometry. In still further alternate embodiments, multiple lancets according to the present invention are joined or packaged together in the form of a cartridge or magazine, such as for example a strip or carousel of lancets that are loaded into the lancing device as a unit and advanced sequentially for individual use.

The lancet of the present invention is manually or automatically loaded into the lancet carrier of a lancing device, with the exposed portion(s) of the shank 24 in direct contact with cooperating positioning guide portion(s) of the lancet carrier. This direct engagement with the shank 24 of the lancet provides tight control of the location of the lancet tip 22, and thus accurate positioning of the lancing site, by eliminating any variation in the spacing d (see FIG. 5) between the lancet tip and the lancet carrier in at least a first dimension. In particular, any dimensional variation resulting from an inconsistent mounting position of the lancet blade within the lancet body of standard lancets is eliminated, because the lancet carrier engages the lancet blade rather than the lancet body. By providing direct engagement between two or more spaced apart exposed portions of the shank 24 and two or more cooperating positioning guides of the lancet carrier 12, tight control of the location of the lancet tip 22, and thus accurate positioning of the lancing site in two or three dimensions, is provided. For example, by providing direct engagement between the lancet blade and the lancet carrier in two spaced apart locations by means of the pin-and-hole connection, the depicted embodiment (seen best with reference to FIG. 5) eliminates positional variation of the lancet tip 22 in both the X and Y-dimensions depicted, and also in the Z-dimension normal to the X and Y-dimensions. The lancet carrier 12, being a reusable component, can be machined or molded using lower-volume tooling and with increased quality control to produce tighter tolerances, whereas the lancet 10 is produced in higher-volume processes for low-cost and disposability after a single-use without adversely affecting the precise locational control of the lancing site.

In an example method of use of the lancet 10 according to the present invention, the lancet is mounted into a lancing device. If provided, the protective endcap or covering is removed. The lancing device is cocked and placed against the subject's skin at the desired lancing site. The lancing device is triggered to drive the lancet tip to penetrate the skin at the sampling site. A sample of blood or other body fluid is expressed from the wound, and the desired sample collection and/or analysis is carried out. After the lancing sequence is carried out, the used lancet may be removed and replaced with a new lancet for further sampling as desired.

Figure 6:
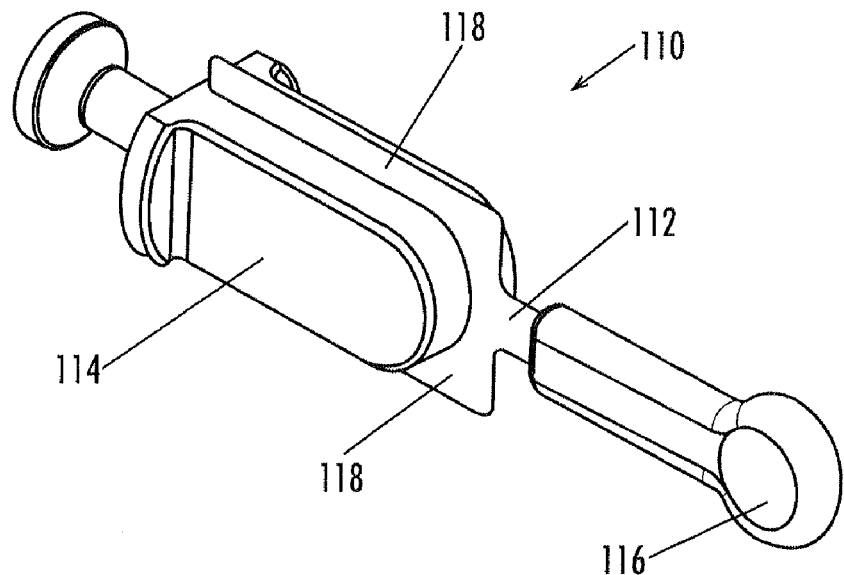
FIG. 6 is a perspective view of a lancet according to another example embodiment of the present invention.
Figure 7:
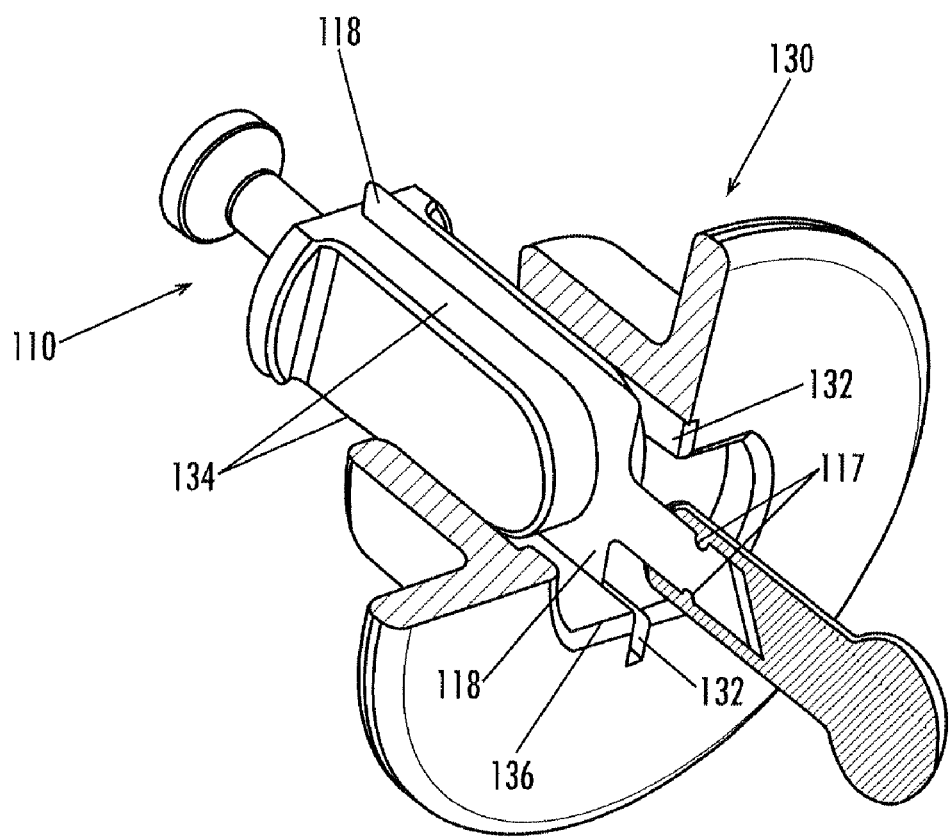
FIG. 7 is a perspective view of the lancet of FIG. 6 engaged in a lancet carrier portion of a lancing device.

Another example embodiment of a lancet 110 according to the present invention is shown in FIGS. 6 and 7. The lancet generally comprises a blade 112 having a plastic body or overmolding 114 and a removable endcap 116 covering the sharp tip of the blade. One or more recesses 117 are optionally formed in the profile of the blade 112 proximal the sharp tip to provide improved retention of the removable endcap 116. A shank portion of the blade 112 comprises one or more exposed wings or projections 118 extending outwardly beyond the body 114. When the lancet 110 is mounted in a lancing device 130, the wings 118 slide in direct engagement within cooperating channels or grooves 132 formed in the lancing device to provide tight guidance of the path of travel of the lancet and precise locational control of the lancing site. Additional guidance of the path of travel of the lancet is optionally provided by sliding contact between one or more guide surfaces 134 of the exterior wall of the lancet body 114 and cooperating guide surfaces 136 of the lancing device 130.

Figure 8:
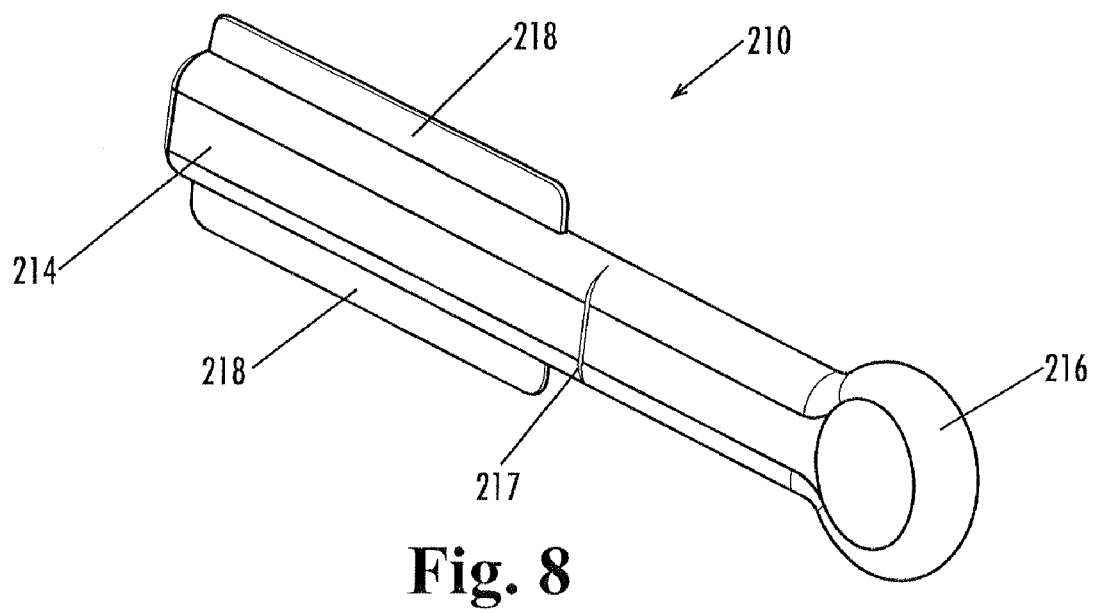
FIG. 8 is a perspective view of a lancet according to still another example embodiment of the present invention.
Figure 9:
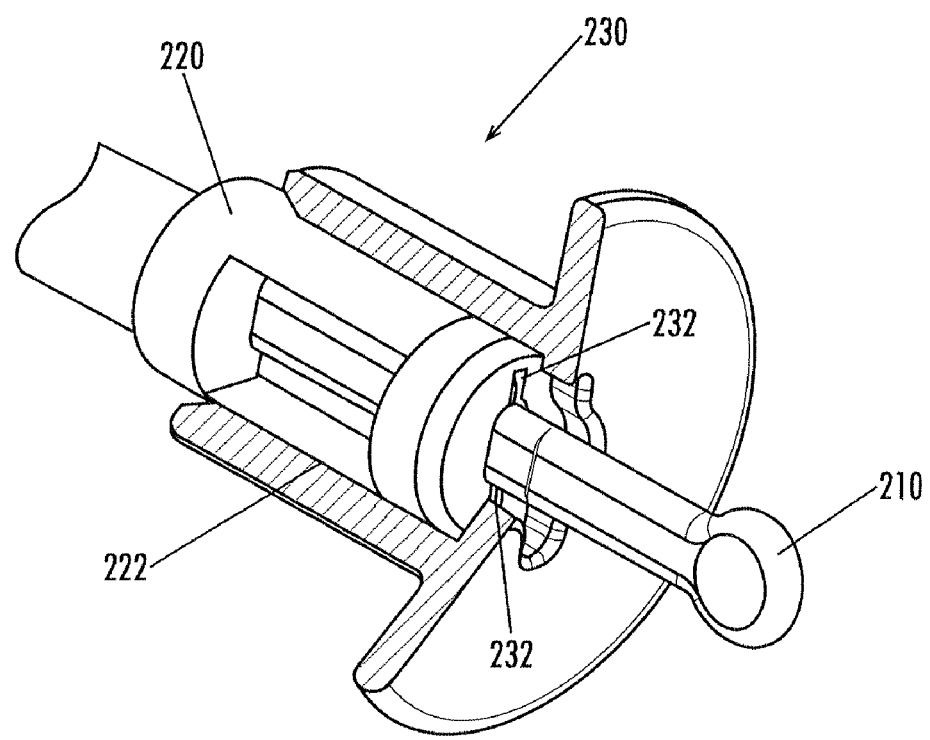
FIG. 9 is a perspective view of the lancet of FIG. 8 engaged in a lancet carrier portion of a lancing device.

FIGS. 8 and 9 show still another embodiment of a lancet 210 according to the present invention. The lancet 210 generally comprises a blade having a plastic body or overmolding 214 with a removable endcap portion 216 covering the sharp tip of the blade. A recess or cut 217 is formed at least partially through the overmolding material to facilitate detachment of the endcap portion 216. A shank portion of the blade comprises one or more exposed wings or projections 218 extending outwardly beyond the body 214. When the lancet 210 is mounted in a lancing device 230, the wings 218 are directly engaged within cooperating channels or grooves 232 in the lancet carrier 220 of the lancing device, and the lancet carrier 220 slides in close engagement within a cooperating guide channel 222 of the housing or other portion of the lancing device, to provide tight guidance of the path of travel of the lancet and precise locational control of the lancing site. Additionally or alternatively, the wings 218 of the lancet blade slide in direct engagement within guide channels or grooves formed in the housing, endcap or other portion of the lancing device 230 to provide precise guidance. The lancet 210 optionally comprises one or more engagement features providing a friction fit or positive locking engagement with the lancet carrier 220 to permit a user to securely but releasably mount the lancet in the lancing device 230.

While the invention has been described with reference to preferred and example embodiments, it will be understood by those skilled in the art that a variety of modifications, additions and deletions are within the scope of the invention, as defined by the following claims.

What is claimed is:

1. A lancing device comprising:
   a lancet carrier comprising a carriage having a resilient arm mounted thereto, a free end of the resilient arm being flexible away from the carriage, and having first and second projections extending from the resilient arm; and
   a lancet for engagement within the lancet carrier, said lancet comprising a lancet blade mounted to a lancet body, the lancet blade comprising a sharp tip and a shank, the lancet body being generally U-shaped with an end panel having two elongated legs extending therefrom in a first direction and the sharp tip of the lancet blade extending therefrom in a second direction generally opposite the first direction, with substantially the entire shank being exposed between the two elongated legs, and wherein the shank comprises a pair of holes through the shank, said holes being spaced a distance from one another and lying along a lengthwise axis of the shank;

wherein the resilient arm flexes away from the carriage to receive and engage the exposed shank of the lancet blade between the two elongated legs of the lancet body, and position the first and second projections of the resilient arm into direct engagement with the pair of holes through the shank.

2. A lancing device for pricking a bodily surface, the lancing device comprising:

a carriage having a resilient arm mounted thereto with a free end of the resilient arm being flexible away from the carriage and having at least one positioning member projecting therefrom;

a lancet for releasable engagement with the carriage, said lancet comprising:

a generally U-shaped body portion having an end panel with two elongated legs extending therefrom in a first direction, and defining an open channel between said two elongated legs for receiving the resilient arm of the lancing device therein; and a lancet blade having an exposed shank extending between the two elongated legs of the body portion, the lancet blade further comprising a sharp tip extending outwardly from the end panel of the body portion in a second direction opposite the first direction, wherein the exposed shank comprises at least one positioning recess for direct engagement with the at least one positioning member of the resilient arm when the lancet is loaded into the lancing device.

* * * * *